(12) United States Patent
Qian et al.

(10) Patent No.: US 12,292,369 B1
(45) Date of Patent: May 6, 2025

(54) INDUCTION TYPE OIL DEBRIS SIGNAL MONITORING AND IDENTIFICATION SYSTEM AND METHOD

(71) Applicants: Suzhou Renzheng Zhitan Technology Co., Ltd., Suzhou (CN); Nanjing University of Aeronautics and Astronautics (NUAA), Nanjing (CN); Nanjing University of Aeronautics and Astronautics Shenzhen Research Institute, Shenzhen (CN)

(72) Inventors: Zhenghua Qian, Nanjing (CN); Guan Wang, Nanjing (CN); Xianwei Wu, Nanjing (CN); Zhi Qian, Nanjing (CN); Peng Li, Nanjing (CN)

(73) Assignees: Nanjing University of Aeronautics and Astronautics (NUAA), Nanjing (CN); Nanjing University of Aeronautics and Astronautics Shenzhen Research Institute, Shenzhen (CN)

( * ) Notice: Subject to any disclaimer, the term of this patent is extended or adjusted under 35 U.S.C. 154(b) by 0 days.

(21) Appl. No.: 18/750,844

(22) Filed: Jun. 21, 2024

(30) Foreign Application Priority Data

Oct. 18, 2023 (CN) .......................... 202311351519.X

(51) Int. Cl.
*G01N 15/06* (2024.01)
*G01N 33/28* (2006.01)
*G06N 20/00* (2019.01)

(52) U.S. Cl.
CPC ..... *G01N 15/0656* (2013.01); *G01N 33/2858* (2013.01); *G06N 20/00* (2019.01)

(58) Field of Classification Search
CPC .... G01N 15/02; G01N 15/0266; G01N 15/06; G01N 15/0656; G01N 33/2858
See application file for complete search history.

(56) References Cited

U.S. PATENT DOCUMENTS

| | | | |
|---|---|---|---|
| 10,233,773 B2 * | 3/2019 | Schwarz | F02C 7/06 |
| 2018/0107203 A1 * | 4/2018 | Hagen | F16N 29/00 |

(Continued)

FOREIGN PATENT DOCUMENTS

| | | | | |
|---|---|---|---|---|
| CA | 2639710 A1 * | 3/2010 | | G01N 33/2858 |
| CN | 113533440 B * | 5/2022 | | |
| WO | WO-2023275372 A1 * | 1/2023 | | G01M 13/021 |

OTHER PUBLICATIONS

Machine translation of WO 2023275372 (Year: 2023).*

(Continued)

*Primary Examiner* — Nathaniel J Kolb
(74) *Attorney, Agent, or Firm* — Getech Law LLC; Jun Ye

(57) ABSTRACT

The present invention provides an induction type oil debris signal monitoring and identification system, which comprises an induction type oil debris sensor, used to detect small electromagnetic changes in the oil and output a monitoring signal after processing through a signal processing circuit; a bubble and debris classification and identification network module, used to analyze whether an abnormal amplitude signal in the monitoring signal contains bubbles or not so as to prevent the bubbles from being c as debris, and a two-level debris signal analysis network module, used to analyze the monitoring signal and determine the size and the quantity of debris.

8 Claims, 5 Drawing Sheets

(56) References Cited

U.S. PATENT DOCUMENTS

| | | | |
|---|---|---|---|
| 2021/0231597 A1* | 7/2021 | Emokpae | G01N 30/02 |
| 2023/0134353 A1* | 5/2023 | Remboski | G01N 33/2888 |
| | | | 73/61.42 |
| 2023/0152298 A1* | 5/2023 | Coupard | F01D 25/20 |
| | | | 324/204 |

OTHER PUBLICATIONS

Machine translation of CN 113533440 (Year: 2022).*
CN 202311351519.X, First Office Action, mailed Apr. 1, 2024, 11 pages. (with English translation).
CN 202311351519.X, Grant of Notice of Patent Right for Invention, mailed May 15, 2024, 3 pages. (with English translation).

* cited by examiner

Excitation Coil 1    INduction Coil    Excitation Coil 2

INDUCTION TYPE OIL DEBRIS SIGNAL MONITORING AND IDENTIFICATION SYSTEM AND METHOD

TECHNICAL FIELD

The present invention relates to the technical field of oil debris signal monitoring and identification, and in particular to an induction type oil debris signal monitoring and identification system and method.

BACKGROUND

When large mechanical equipment such as engines and turbines are running, friction and relative motion between parts will inevitably lead to working surface wear of the parts. The lubricating oil system can provide necessary lubrication for the parts of the mechanical equipment, while the tiny particles produced by wear will flow with lubricating oil in the system.

By analyzing the size, concentration and other parameters of metal particles in lubricating oil, the health status and degree of wear of the parts can be objectively reflected. This allows us to detect the wear problems of the mechanical parts early and issue alarms in advance, thereby effectively preventing the occurrence of major accidents.

In order to monitor the debris in the lubricating oil system, the induction type oil debris detection technology is widely used. The technology takes advantage of the fact that metal particles in the oil can interfere with electromagnetic fields, and this interference is detected and output by an internal induction coil. At present, the induction type lubricating oil debris sensor mostly identifies the debris through amplitude identification, that is, when the signal exceeds certain amplitude, the debris is recorded. This method has two problems. First, there is a large amount of gas mixed in the oil, but this does not affect the operation of the equipment. Due to the different magnetic permeability of gas and oil, induction signals will also be output when bubbles pass through the sensor. The amplitude identification method will mistakenly identify the bubble signal as debris, causing the number of debris records to increase; secondly, when the equipment is working in the running-in period and the stable period, the debris generated is mainly single particle and small-size particles. However, when the bearing is working at the end of the stable period and the failure period, multiple large-size debris may be produced by single wear, and multiple large-size debris passes through the sensor at small intervals. However, existing research shows that when the distance between the debris is less than 25 mm, the debris signals will superimpose each other, and the large-size debris signals will also cover up the small-size debris signals. The above reasons will cause quantity measurement errors; when two debris signals are superimposed in a certain special phase relationship, the peak-to-peak values of the signals will even be weakened, causing errors in the measurement of debris size. To sum up, the induction type lubricating oil monitoring urgently needs a method to accurately measure the quantity and size of debris.

SUMMARY

The present invention provides an induction type oil debris signal monitoring and identification system and method. The purpose is to improve the accuracy of monitoring and identifying the oil debris and replace the traditional debris counting method by depending on the signal amplitude; the problem that signal interference is generated when mixed bubbles exist in the oil is solved; the problems of aliasing signal counting and size identification when a plurality of particles pass through at small intervals are solved; the accuracy of signal identification and the automation degree of the monitoring system are improved.

The first aspect of this description discloses an induction type oil debris signal monitoring and identification system, which comprises:

the induction type oil debris sensor, used to detect the small electromagnetic changes in the oil, and output the monitoring signal after processing through the signal processing the bubble and dust classification and identification network module, used to analyze whether the abnormal amplitude signal in the monitoring signal contains bubbles or not so as to prevent the bubbles from being mistakenly identified as debris;

the two-level debris signal analysis network module, used to analyze the monitoring signal and determine the size and quantity of the debris.

In the embodiment disclosed in this description, the induction type oil debris sensor is wound on the ceramic frame through the enameled wire, forming two inverse parallel excitation coils and an electromagnetic induction coil; the electromagnetic induction coil outputs the small electrical signal, and then the signal is amplified, self-multiplied, demodulated and filtered through the signal processing circuit, and then the monitoring signal is output.

In the embodiment disclosed in this description, the bubble and debris classification and identification network module is based on the back propagation neural network, and trained by inputting the oil bubble signal and the debris signal to achieve automatic separation of the bubbles and the debris.

In the embodiment disclosed in this description, the two-level debris signal analysis network module is based on the back propagation neural network and constructed using the two-level network analysis method; the first-level network in the two-level debris signal analysis network module identifies the quantity of the debris in the monitoring signal, and the second-level network in the two-level debris signal analysis network module identifies the size of the debris in the monitoring signal.

In the embodiment disclosed in this description, the second-level network includes single debris size identification network, double debris size identification network and triple debris size identification network.

The second aspect of this description discloses an induction type oil debris signal monitoring and identification method, including:

S1. Detecting the small electromagnetic changes in the oil, and outputting the monitoring signal after signal processing;

S2. Extracting and analyzing the abnormal amplitude signal in the monitoring signal; if the abnormal amplitude signal is a bubble signal, it will not be included in the quantity of the debris; if the abnormal amplitude signal is a debris signal, then the monitoring signal will undergo two-level debris signal analysis;

S3. During the two-level debris signal analysis, first identifying the quantity of the debris in the monitoring signal; if it is identified to be single debris, then identifying the size of the single debris; if it is identified to be double debris, then identifying the size of the double debris; if it is identified to be triple debris, then identifying the size of the triple debris;

S4. Recording the quantity and size of the debris.

In the embodiment disclosed in this description, the induction type oil debris signal monitoring and identification method is implemented by the above induction type oil debris signal monitoring and identification system.

In the embodiment disclosed in this description, the model training process of the bubble and debris classification and identification network module is as follows:

A1. Collection of bubble and debris training signals:

A11. Collecting bubble signals:

Use the pinhole to inject bubbles of different sizes into the oil, and collect bubble signals repeatedly until the training requirements are met, that is, the diversity of the collected signals is ensured by random changes in the bubble size;

A12. Collecting debris signals:

The debris signal randomly uses single debris signal, double debris signal and triple debris signal to ensure the diversity of collected signals, and the number of debris signals collected is consistent with that of bubble signals collected;

After the bubble signal and debris signal are collected, labels are set for the bubble signal and debris signal respectively to obtain the first collected data;

A2. Bubble and debris classification and identification model training:

Use the BP algorithm Matlab toolbox for model training;

The training data is randomly selected from ⅓ of all the first collected data and divided into training set, verification set and test set in a ratio of 7:2:1; the training learning rate is a dynamic learning rate; during the training process, different numbers of hidden layers and nodes are selected to repeat the training, and the best model is determined based on the comprehensive accuracy rate and network size.

In the embodiment disclosed in this description, the model training process of the two-level debris signal analysis network module is as follows:

B1. Collection of debris training signals:

Collect the signals multiple times for single-particle, double-particle, and triple-particle debris to obtain the second collected data;

B2. Training of the debris quantity identification model:

Use the BP algorithm Matlab toolbox for model training;

The training data is randomly selected from ⅓ of all the second collected data and divided into training set, verification set and test set in a ratio of 7:2:1, and the training learning rate is a dynamic learning rate; the optimal number of hidden layers and nodes are selected through multiple tests, and the best results are selected to determine the best model.

In the embodiment disclosed in this description, when the debris training signal is collected, 100 sampling points are intercepted from the signal to maintain integrity, and the interception point is located in the middle of the peak and valley time points of the signal.

To sum up, the present invention at least has the following beneficial effects:

The prevent invention can accurately identify whether the abnormal amplitude signal contains bubbles, and then accurately count the quantity of the debris. It can accurately analyze the quantity and size of the debris contained in the debris signal, and avoid the omission in recording the quantity of the debris caused by small debris intervals, size analysis errors, and other problems.

The signal monitoring accuracy of the present invention is high, and the sensor and signal processing circuit can amplify the induced electrical signal at the microvolt level by 30,000 times without distortion, which facilitates subsequent signal processing.

Compared with the traditional signal amplitude debris counting method, the accuracy of debris identification, the accuracy of quantity identification, and the accuracy of size identification can reach 99.3%, 97.1%, and 97.6%, respectively.

BRIEF DESCRIPTION OF DRAWINGS

In order to illustrate the technical solutions in the embodiments of the present invention more clearly, the accompanying drawings to be used in the description of the embodiments will be introduced briefly below. It is apparent that the accompanying drawings in the following description are only some of the embodiments of the present invention. For those of ordinary skill in the art, other accompanying drawings can further be obtained according to these accompanying drawings without any creative efforts.

EMBODIMENTS

In the following, only some exemplary embodiments are briefly described. As those skilled in the art would realize, the described embodiments may be modified in various different ways, all without departing from the spirit or scope of the present invention. Accordingly, the drawings and descriptions are to be regarded as illustrative in nature and not restrictive.

The following disclosure provides many different embodiments or examples for implementing different structures of the embodiments of the present invention. To simplify the disclosure of embodiments of the present invention, components and arrangements of specific examples are described below. Of course, they are merely examples and are not intended to limit the embodiments of the present invention. Furthermore, the embodiments of the present invention may repeat reference numbers and/or reference letters in different examples, such repetition being for purposes of simplicity and clarity and does not in itself indicate a relationship between the various embodiments and/or arrangements discussed.

The embodiments of the present invention will be described in detail below with reference to the accompanying drawings.

Figure 1:
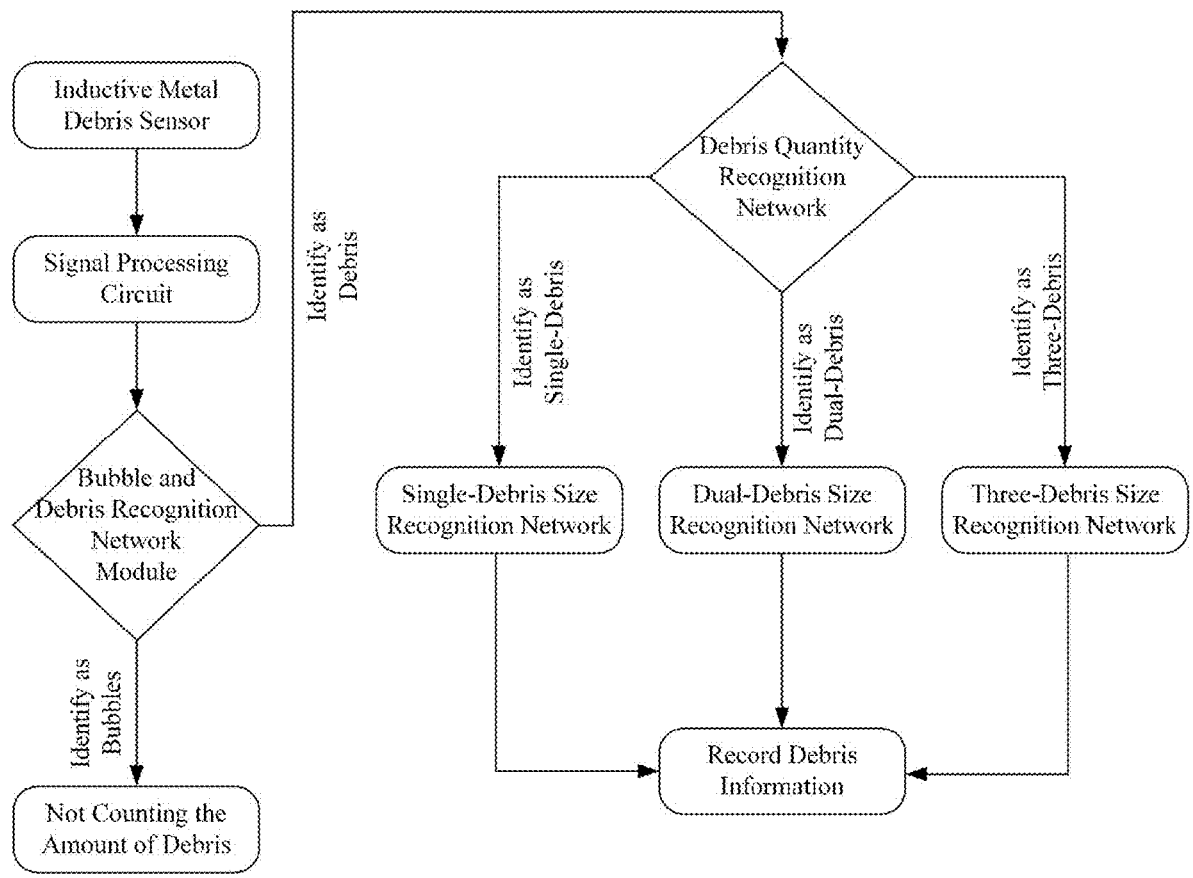
FIG. 1 is a schematic flow chart of the induction type oil debris signal monitoring and identification system and method involved in the present invention.

As shown in FIG. 1, the first aspect of this description discloses an induction type oil debris signal monitoring and identification system, which comprises:

the induction type oil debris sensor, used to detect the small electromagnetic changes in the oil, and output the monitoring signal after processing through the signal processing the bubble and dust classification and identification network module, used to analyze whether the abnormal amplitude signal in the monitoring signal contains bubbles or not so as to prevent the bubbles from being mistakenly identified as debris;

the two-level debris signal analysis network module, used to analyze the monitoring signal and determine the size and quantity of the debris.

Figure 2:
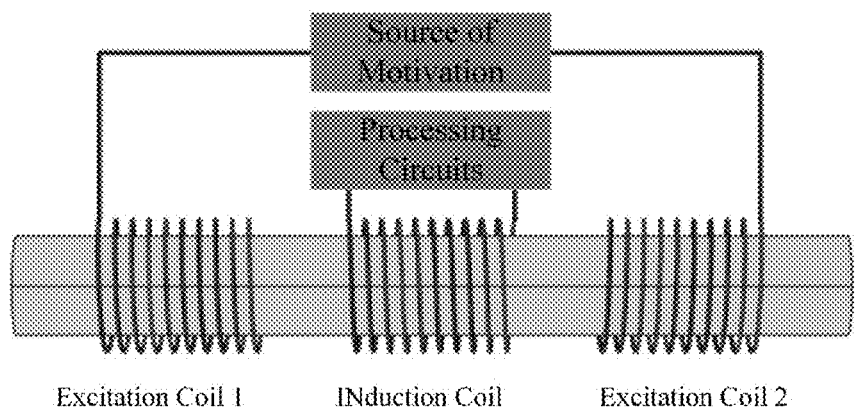
FIG. 2 is a schematic diagram of the induction type oil debris sensor involved in the present invention.

In some embodiments, as shown in FIG. 2, the induction type oil debris sensor is wound on the ceramic frame through the enameled wire, forming two inverse parallel excitation coils and an electromagnetic induction coil; the electromagnetic induction coil outputs the small electrical signal, and then the signal is amplified, self-multiplied, demodulated and filtered through the signal processing circuit, and then the monitoring signal is output.

The excitation coil is used to generate a stable magnetic field, and the two excitation coils are connected in reverse parallel to the same AC current source; the induction coil is used to receive the magnetic field change signal in the sensor and output a small electrical signal.

In some embodiments, the bubble and debris classification and identification network module is based on the back-propagation neural network and is trained by inputting the oil bubble signal and the debris signal to realize automatic separation of the bubbles and the debris.

In some embodiments, the two-level debris signal analysis network module is based on the back propagation neural network and constructed using the two-level network analysis method; the first-level network in the two-level debris signal analysis network module identifies the quantity of the debris in the monitoring signal, and the second-level network in the two-level debris signal analysis network module identifies the size of the debris in the monitoring signal.

In some embodiments, the second-level network includes single debris size identification network, double debris size identification network and triple debris size identification network.

As shown in FIG. 1, the second aspect of this description discloses an induction type oil debris signal monitoring and identification method, including:

S1. Detecting the small electromagnetic changes in the oil, and outputting the monitoring signal after signal processing;

S2. Extracting and analyzing the abnormal amplitude signal in the monitoring signal; if the abnormal amplitude signal is a bubble signal, it will not be included in the quantity of the debris; if the abnormal amplitude signal is a debris signal, then the monitoring signal will undergo two-level debris signal analysis;

S3. During the two-level debris signal analysis, first identifying the quantity of debris in the monitoring signal; if it is identified to be single debris, then identifying the size of the single debris; if it is identified to be double debris, then identifying the size of the double debris; if it is identified to be triple debris, then identifying the size of the triple debris;

S4. Recording the quantity and size of the debris.

In some embodiments, the induction type oil debris signal monitoring and identification method is implemented by the above induction type oil debris signal monitoring and identification system.

Figure 3:
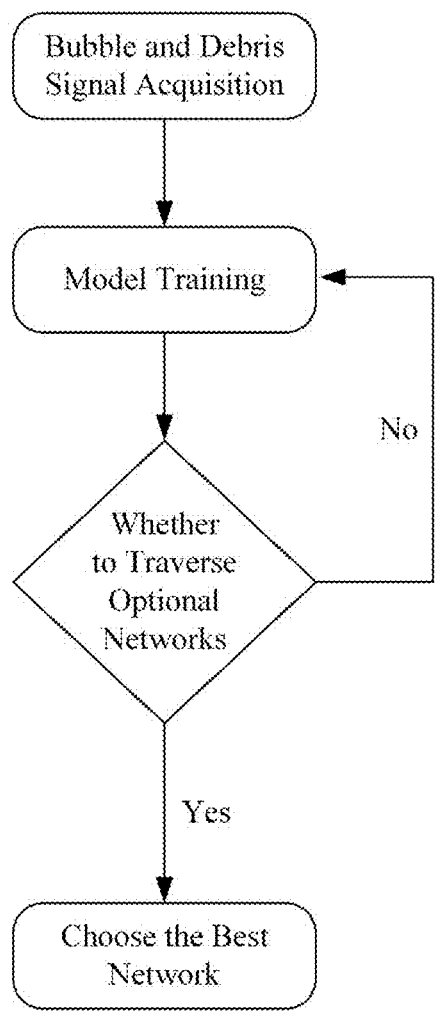
FIG. 3 is a schematic diagram of the model training process of the bubble and debris classification and identification network module involved in the present invention.

In some embodiments, as shown in FIG. 3, the model training process of the bubble and debris classification and identification network module is as follows:

Training signal collection: model training requires the collection of abundant bubble signals and debris signals. The size of bubbles in the oil changes randomly. According to the actual situation, the pinhole is used to inject bubbles of different sizes into the oil, and the collection is repeated multiple times until the training requirements are met. The debris signals are randomly collected using single debris, double debris, and triple debris to ensure signal diversity. The number of collected signals is consistent with the number of bubble signals. After the collection of bubble signals and debris signals is completed, labels are set for the signals for the next step of training.

Model training: model training is performed using the BP algorithm Matlab toolbox. The training data is randomly selected from ⅓ of all the data and divided into training set, verification set and test set in a ratio of 7:2:1, and the training learning rate is a dynamic learning rate; there is no limit on the training time. During the training process, different numbers of hidden layers and nodes are selected to repeat the training, and the best model is determined based on the comprehensive accuracy rate and network size.

In short, through training signal collection, signal type marking, and model training, the structure with the highest accuracy is selected as the final model. The specific steps are as follows:

A1. Collection of bubble and debris training signals:

A11. Collecting bubble signals:

Use the pinhole to inject bubbles of different sizes into the oil, and collect bubble signals repeatedly until the training requirements are met, that is, the diversity of the collected signals is ensured by random changes in the bubble size;

A12. Collecting debris signals:

The debris signal randomly uses single debris signal, double debris signal and three-particle debris signal to ensure the diversity of collected signals, and the number of debris signals collected is consistent with that of bubble signals collected;

After the bubble signal and debris signal are collected, labels are set for the bubble signal and debris signal respectively to obtain the first collected data;

A2. Bubble and debris classification and identification model training:

Use the BP algorithm Matlab toolbox for model training;

The training data is randomly selected from ⅓ of all the first collected data and divided into training set, verification set and test set in a ratio of 7:2:1; the training learning rate is a dynamic learning rate; during the training process, different numbers of hidden layers and nodes are selected to repeat the training, and the best model is determined based on the comprehensive accuracy rate and network size; that is, traverse all available networks and select the best network.

Figure 4:
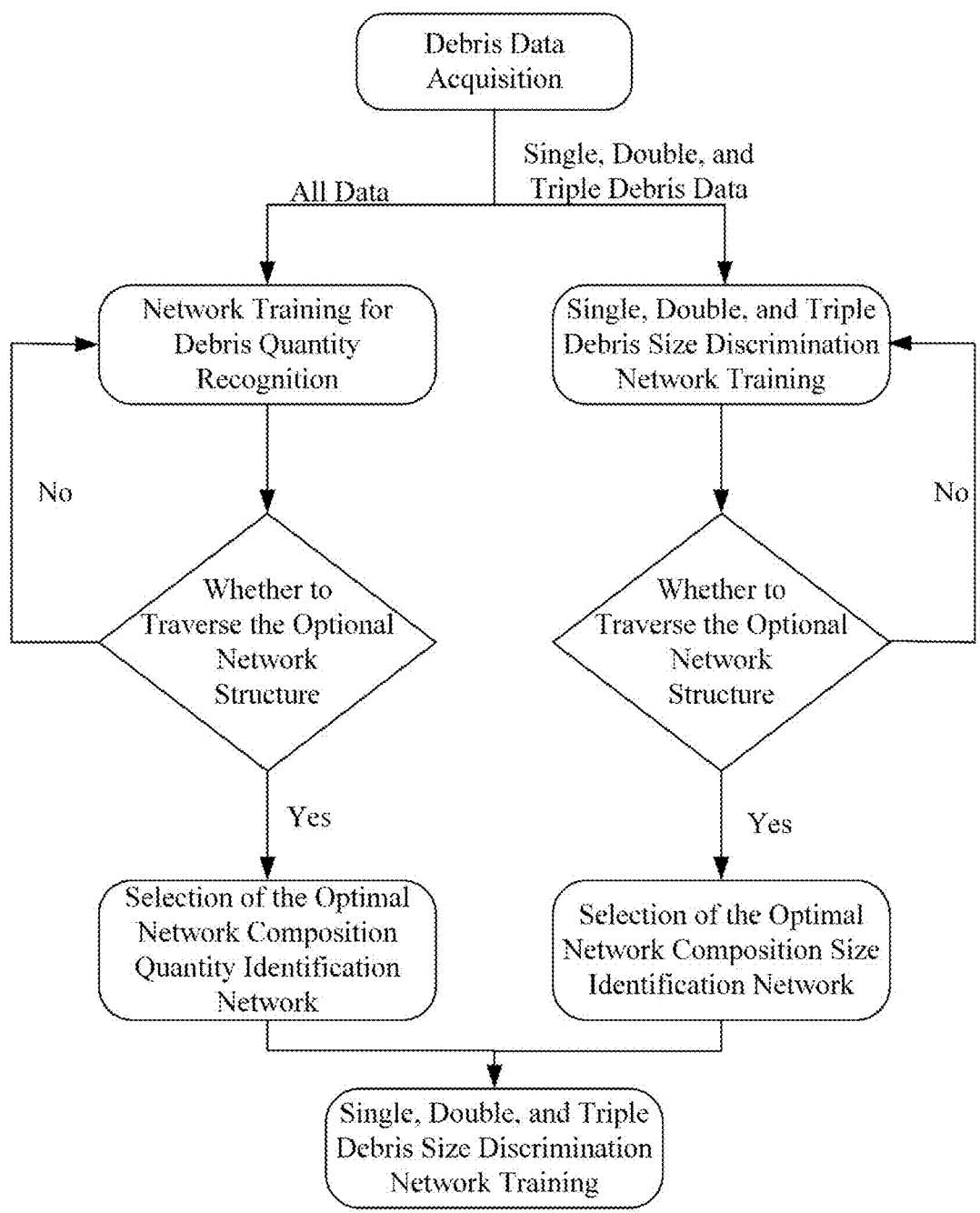
FIG. 4 is a schematic diagram of the model training process of the two-level debris signal analysis network module involved in the present invention.

In some embodiments, as shown in FIG. 4, the training process of the model of the two-level debris signal analysis network module (two-level multi-debris information identification model) is as follows:

Training signal collection: model training requires sufficient training data, and the signal collection process needs to consider both single and multiple particles. In multi-particle scenarios, double particles are the most common, followed by triple particles, while four or more particles are very rare. Therefore, signal collection is performed separately for single particles, double particles, and triple particles. When collecting signals, the debris will be collected multiple times through the sensor, and the double particles and triple particles need to be collected according to the particle size ratio and interval. The particle size ranges from 100 microns to 300 microns and is evenly spaced from 3 mm to 20 mm. Special attention is paid to the collection of multi-particle signals considering various combinations of particle diameter ratios and spacing.

For quantity identification model training, a complete debris signal contains 70 sampling points, so 100 sampling points are intercepted from the signal to maintain integrity. The interception point is located in the middle of the signal peak and valley time points. The signal label is used for the desired output of the training data, where the quantity model has only one label, representing the number of particles. Since the expected signal contains at most 3 particles, three models are needed to determine the particle diameter, so the model label includes the debris diameter.

Quantity identification model training: model training is performed using the BP algorithm Matlab toolbox. The training data is randomly selected from ⅓ of all the data and divided into training set, verification set and test set in a ratio of 7:2:1, and the training learning rate is a dynamic learning rate; there is no limit on the training time. Different network structures will have a significant impact on the training results. Too few layers and nodes may lead to underfitting, while too many layers and nodes may lead to overfitting, affecting the quality of the network. Multiple tests are required to select the best number of hidden layers and nodes. The available network structures include 1-4 layers, with the number of nodes in each layer being 80, 100, 120 and 140 respectively. The network of each structure is trained 30 times, and the best result is selected as the final network.

In short, training data is obtained by collecting a large number of signals of single debris, double debris, and triple debris, and labeling the number and size of each group of chips. The quantity identification model and the size (diameter) identification model are trained in sequence, and the structure with the maximum accuracy is selected as the final model (quantity identification network and diameter identification network). The specific steps are as follows:

B1. Collection of debris training signals:
 Collect the signals multiple times for single, double, and triple debris to obtain the second collected data;
B2. Training of debris quantity identification model and single/double/triple debris size identification model:
 Use the BP algorithm Matlab toolbox for model training;
 The training data is randomly selected from ⅓ of all the second collected data and divided into training set, verification set and test set in a ratio of 7:2:1, and the training learning rate is a dynamic learning rate; the optimal number of hidden layers and nodes are selected through multiple tests, and the best results are selected to determine the best model. That is, the debris quantity identification model and the single/double/triple debris size identification model (single debris size identification network, double chip size identification network and triple debris size identification network) are obtained respectively.

Figure 5:
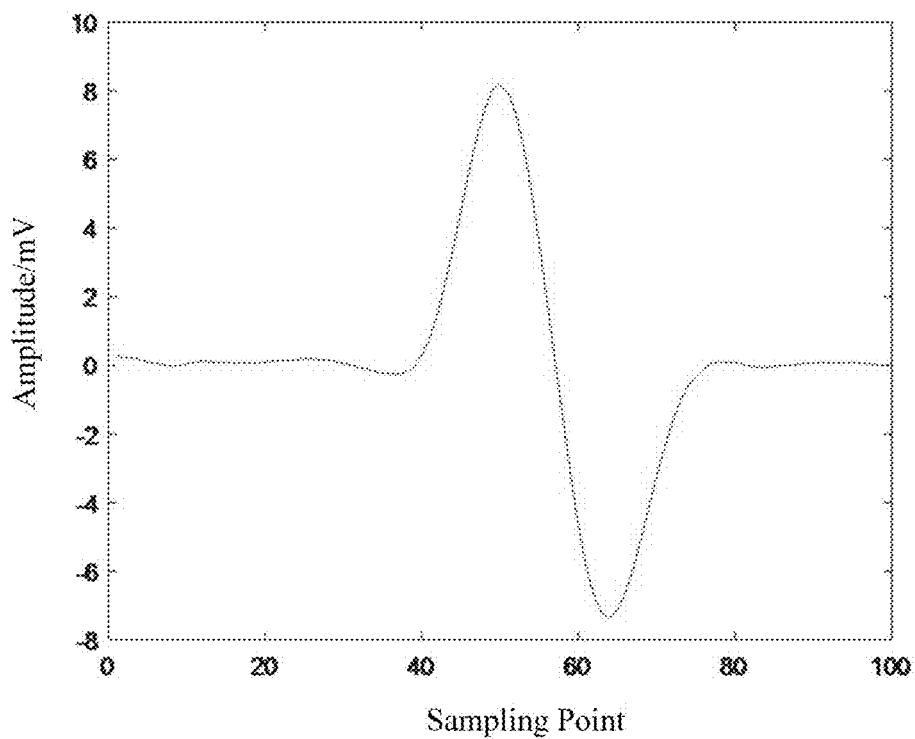
FIG. 5 is a schematic diagram of collecting 204 micron single debris signals involved in the present invention.
Figure 6:
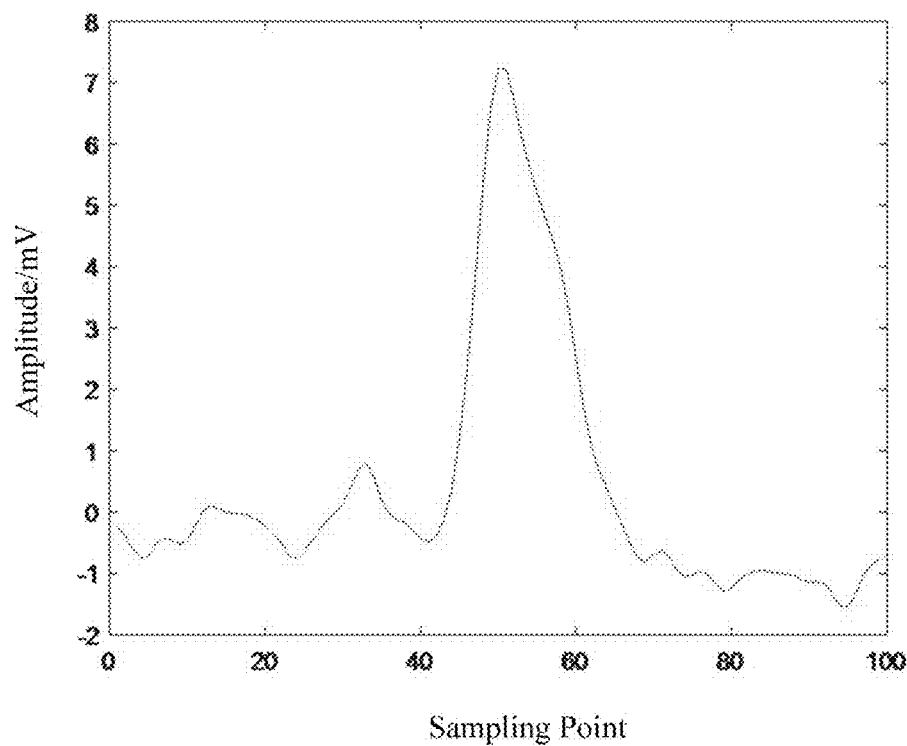
FIG. 6 is a schematic diagram of collecting bubble signals involved in the present invention.
Figure 7:
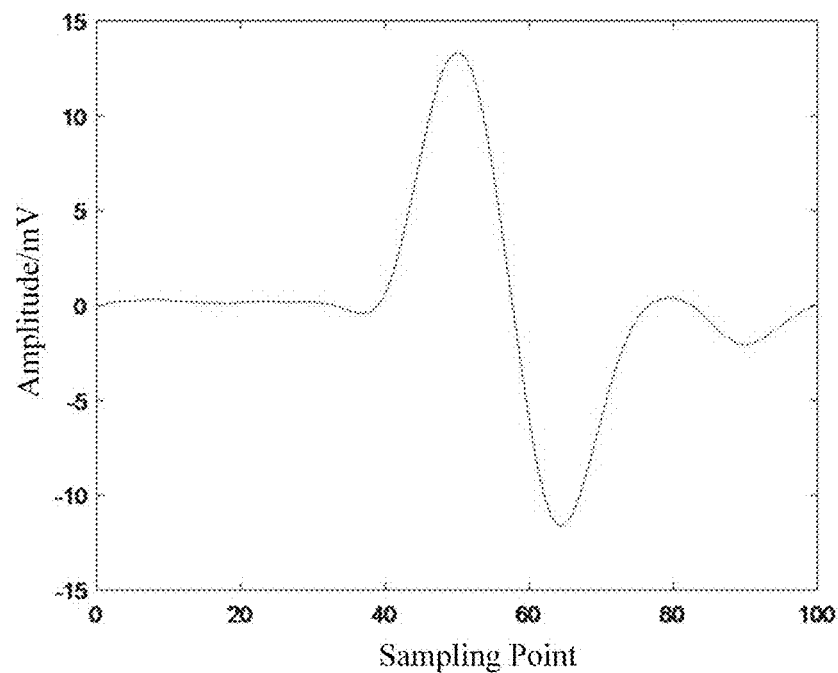
FIG. 7 is a schematic diagram of collecting triple debris signals composed of 233, 108, and 131 micron debris involved in the present invention.

In some embodiments, as shown in FIG. 5, FIG. 6 and FIG. 7, when the debris training signal is collected, 100 sampling points are intercepted from the signal to maintain integrity, and the interception point is located in the middle of the peak and valley time points of the signal.

In summary, the induction type oil debris sensor detects the small electromagnetic changes in the oil, and outputs the monitoring signal by processing through the signal processing circuit; the bubble and debris classification and identification network module analyzes whether the abnormal amplitude signal in the monitoring signal contains bubbles to prevent the bubbles from being mistakenly identified as debris; when it is identified as bubbles, they will not be included in the quantity of debris; when it is identified as debris, the monitoring signal is sent to the two-level debris signal analysis network module to analyze the monitoring signal and determine the size and quantity of debris; wherein, it is first executed by the debris quantity identification network, and the quantity of debris is identified by the debris quantity identification network. When it is identified as single debris, the monitoring signal is sent to the single debris size identification network; when it is identified as double debris, the monitoring signal is sent to the double debris size identification network; when it is identified as triple debris, the monitoring signal is sent to the triple debris size identification network; after the quantity and size identification is completed, the debris information is recorded.

In summary, the present invention has highly accurate signal monitoring and signal identification capabilities. The system's sensors and signal processing circuits can amplify weak induced electrical signals with low distortion and high magnification; in addition, the system can also accurately identify whether bubbles are included in abnormal amplitude signals, with an accuracy of 99.3%, thus ensuring accurate counting of the debris. Unlike traditional amplitude-based technical methods, this system does not mistakenly identify bubbles as debris, thereby avoiding counting errors. In addition, the system can also accurately analyze the quantity and size of debris contained in the debris signal, avoiding problems such as omission in recording the debris and size analysis errors caused by small intervals between debris, and quantity and size identification accuracy rate can reach 97.1%, and 97.6%, respectively. Therefore, the system can be widely used in aircraft engine oil systems, large turbines and other mechanical equipment lubrication systems for online detection of metal debris.

The above embodiments are used to illustrate the present invention, but not to limit the present invention. Therefore, changes in the numerical values or replacement of equivalent components should still fall within the scope of the present invention.

From the above detailed description, those of ordinary skill in the art can understand that the present invention can indeed achieve the aforementioned objects and is in compliance with the provisions of the patent law.

Although the preferred embodiments of the present invention have been described, those skilled in the art will be able to make additional changes and modifications to these embodiments once the basic inventive concepts are apparent. Therefore, it is intended that the appended claims be construed to include the preferred embodiments and all changes and modifications that fall within the scope of the invention. The above descriptions are only preferred embodiments of the present invention and are not intended to limit the present invention. It should be noted that any modifications, equivalent substitutions, improvements, etc. made within the spirit and principles of the present invention shall be included within the scope of protection of the present invention.

It should be noted that the above description of the relevant processes is only for example and explanation, and does not limit the scope of application of this description. For those skilled in the art, various modifications and changes can be made to the process under the guidance of this description. However, such modifications and changes remain within the scope of this description.

The basic concepts have been described above. It is obvious to those of ordinary skill in the art after reading this application that the above disclosure of the invention is only an example and does not constitute a limitation on this application. Although not explicitly stated herein, various modifications, improvements, and corrections to the present application may be made by those of ordinary skill in the art. Such modifications, improvements and corrections are suggested in this application, so such modifications, improvements and corrections still fall within the spirit and scope of the exemplary embodiments of this application.

At the same time, this application uses specific words to describe the embodiments of the application. For example, "one embodiment," "an embodiment," and/or "some embodiments" means a certain feature, structure, or characteristic related to at least one embodiment of the present application. Therefore, it should be emphasized and noted that "an embodiment" or "one embodiment" or "an alternative embodiment" mentioned twice or more at different places in this description does not necessarily refer to the same embodiment. In addition, certain features, structures or characteristics in one or more embodiments of the present application may be appropriately combined.

Furthermore, those of ordinary skill in the art will appreciate that aspects of the present application may be illustrated and described in several patentable categories or circumstances, including any new and useful process, machine, product, or combination of matter, or for any new and useful improvements to it. Therefore, various aspects of the present application may be implemented entirely by hardware, may be entirely implemented by software (including firmware, resident software, microcode, etc.), or may be implemented by a combination of hardware and software. The above hardware or software may be called "units", "modules" or "systems". Additionally, aspects of the present application may take the form of a computer program product embodied in one or more computer-readable media, with computer-readable program code embodied therein.

The computer program code required for the operation of each part of this application can be written in any one or more programming languages, including object oriented programming languages such as Java, Scala, Smalltalk, Eiffel, JADE, Emerald, C++, C#, VB.NET, and Python, conventional programming languages such as C programming language, Visual Basic, Fortran2103, Perl, COBOL2102, PHP, ABAP, dynamic programming languages such as Python, Ruby and Groovy or other programming languages. The program code may run entirely on the user's computer, as a stand-alone software package, partially on the user's computer and partially on a remote computer, or entirely on the remote computer or server. In the latter case, the remote computer can be connected to the user computer via any form of network, such as a local area network (LAN) or a wide area network (WAN), or to an external computer (e.g. via the Internet), or in a cloud computing environment, or as a service use such as software as a service (SaaS).

In addition, unless explicitly stated in the claims, the order of the processing elements and sequences described in this application, the use of numbers and letters, or the use of other names are not used to limit the order of the processes and methods of this application. Although the foregoing disclosure discusses by various examples some embodiments of the invention that are presently considered useful, it is to be understood that such details are for purposes of illustration only and that the appended claims are not limited to the disclosed embodiments. On the contrary, the claims are intended to cover all modifications and equivalent combinations consistent with the spirit and scope of the embodiments of the application. For example, while the implementation of the various components described above may be embodied in a hardware device, it may also be implemented as a purely software solution, such as an installation on an existing server or mobile device.

Similarly, it should be noted that in order to simplify the presentation of the disclosure of the present application and thereby facilitate understanding of one or more embodiments of the invention, in the foregoing description of the embodiments of the present application, multiple features are sometimes combined into one embodiment, drawings or descriptions thereof. This approach to this application is not to be interpreted, however, as reflecting an intention that the claimed subject matter requires more features than are expressly recited in each claim. On the contrary, the subject matter of the invention should have fewer features than a single embodiment described above.

The invention claimed is:

1. An induction type oil debris signal monitoring and identification method, which is characterized by including:
   detecting electromagnetic changes in oil, and outputting a monitoring signal after signal processing;
   extracting and analyzing an amplitude from the monitoring signal;
     wherein if the amplitude is a bubble signal, it will not be included in the quantity of debris;
       wherein analyzing, by a bubble and debris classification and identification network module, if the amplitude is a bubble signal comprises basing the bubble and debris classification and identification network module on a back propagation (BP) neural network, and training the bubble and debris classification and identification network module by inputting an oil bubble signal and a debris signal to achieve automatic separation differentiation of the bubbles and the debris;
     wherein if the amplitude is a debris signal, then analyzing the monitoring signal with a two-level debris signal analysis;
   during the two-level debris signal analysis, first identifying the quantity of the debris in the monitoring signal;
     wherein if it is identified to be a single quantity of debris, then identifying the size of the single quantity of debris;
     wherein if it is identified to be a double quantity of debris, then identifying the respective sizes of the double quantity of debris; and
     wherein if it is identified to be a triple quantity of debris, then identifying the respective sizes of the triple quantity of debris; and
   recording the quantity or quantities and size or sizes of the debris.

2. An induction type oil debris signal monitoring and identification method according to claim 1, further comprising:
   detecting, by an induction type oil debris sensor, the electromagnetic changes in the oil, and outputting the monitoring signal after processing through a signal processing circuit; and
   analyzing, by a two-level debris signal analysis network module, the monitoring signal and determining the size and quantity of the debris.

3. The induction type oil debris signal monitoring and identification method according to claim 2, further comprising:
- collecting, by the bubble and debris classification and identification network module, bubble and debris training signals comprising:
  - collecting bubble signals including: using a pinhole to inject bubbles of different sizes into the oil, and collecting bubble signals to ensure diversity of the collected signals;
  - collecting debris training signals is as follows: randomly using single quantity debris, double quantity debris, or triple quantity debris in the oil, and collecting debris training signals to ensure the diversity of the collected signals; and
  - setting labels for the bubble signal and debris training signals respectively to obtain the first collected data; and
- wherein the-bubble and debris classification and identification model training includes:
- using a BP algorithm toolbox for model training; and
- randomly selecting training data from ⅓ of all the first collected data and dividing into a training set, a verification set and a test set in a ratio of 7:2:1; wherein a training learning rate is a dynamic learning rate; and during the training process, selecting different numbers of hidden layers and nodes to repeat the training, and determining a best model based on a comprehensive accuracy rate and network size.

4. The induction type oil debris signal monitoring and identification method according to claim 2, further comprising:
- collecting, by the two level debris signal analysis module, debris training signals including:
  - collecting the signals multiple times is as follows: randomly using single-particle, double-particle, and triple-particle debris in the oil, and collecting debris training signals to obtain a second collected data; and
- training the debris quantity identification model including:
  - using a BP algorithm toolbox for model training; and
  - randomly selecting training data from ⅓ of all the second collected data and dividing into a training set, a verification set and a test set in a ratio of 7:2:1, wherein a training learning rate is a dynamic learning rate; and selecting an optimal number of hidden layers and nodes through multiple tests, and selecting best results to determine a best model based on a comprehensive accuracy rate and network size.

5. The induction type oil debris signal monitoring and identification method according to claim 4, characterized in that when the debris training signal is collected, intercepting 100 sampling points from the signal, and locating interception points in the middle of peak and valley time points of the signal.

6. The induction type oil debris signal monitoring and identification method according to claim 2, wherein
- the induction type oil debris sensor comprises an enameled wire wound on a ceramic frame, forming two inverse parallel excitation coils and an electromagnetic induction coil; and
- outputting an electrical signal from the electromagnetic induction coil, and amplifying, self-multiplying, demodulating and filtering the signal through the signal processing circuit, and outputting the monitoring signal.

7. The induction type oil debris signal monitoring and identification method according to claim 2, wherein
- basing the two-level debris signal analysis network module on a back propagation neural network, and
- constructing the two-level debris signal analysis network module using a two-level network analysis method; wherein
  - using a first-level network in the two-level debris signal analysis network module to identify the quantity of the debris in the monitoring signal, and using a second-level network in the two-level debris signal analysis network module to identify the size of the debris in the monitoring signal.

8. The induction type oil debris signal monitoring and identification method according to claim 7, wherein the second-level network further includes using a single debris size identification network, a double debris size identification network and a triple debris size identification network.

* * * * *